United States Patent [19]
Gustafson

[11] Patent Number: 5,817,644
[45] Date of Patent: Oct. 6, 1998

[54] TARGETING OF DOSAGES OF MEDICINE AND THERAPEUTIC AGENTS

[75] Inventor: Stefan Gustafson, Mississauga, Canada

[73] Assignee: Hyal Pharmaceutical Corporation, Mississauga, Canada

[21] Appl. No.: 568,489

[22] Filed: Dec. 7, 1995

Related U.S. Application Data

[63] Continuation-in-part of Ser. No. 675,908, Jul. 3, 1991, and Ser. No. 468,328, Jun. 6, 1995, and a continuation-in-part of Ser. No. 520,591, Aug. 30, 1995.

[51] Int. Cl.$^6$ .................................................. A61K 31/70
[52] U.S. Cl. ............................................ 514/54; 514/62
[58] Field of Search ........................................ 514/54, 62

[56] References Cited

U.S. PATENT DOCUMENTS

| | | | |
|---|---|---|---|
| 2,583,096 | 1/1952 | Hadidian et al. | 536/55.1 |
| 3,436,454 | 4/1969 | Nouvel | 514/54 |
| 3,887,703 | 6/1975 | Manoussos et al. | 424/581 |
| 4,141,973 | 2/1979 | Balazs | 514/54 |
| 4,272,522 | 6/1981 | Balazs | 424/94.61 |
| 4,582,865 | 4/1986 | Balazs et al. | 514/29 |
| 4,636,524 | 1/1987 | Balazs et al. | 514/781 |
| 4,711,780 | 12/1987 | Fahim | 424/641 |
| 4,716,224 | 12/1987 | Sakurai et al. | 536/55.1 |
| 4,725,585 | 2/1988 | Wenge et al. | 514/54 |
| 4,736,024 | 4/1988 | Della Valle et al. | 536/55.3 |
| 4,755,544 | 7/1988 | Makino et al. | 524/42 |
| 4,795,741 | 1/1989 | Leshchiner et al. | 514/21 |
| 4,801,619 | 1/1989 | Lindblad | 514/42 |
| 4,808,576 | 2/1989 | Schultz et al. | 514/54 |
| 4,814,176 | 3/1989 | Makino et al. | 424/457 |
| 4,840,941 | 6/1989 | Ueno et al. | 514/59 |
| 4,851,521 | 7/1989 | della Valle et al. | 536/55.1 |
| 4,853,226 | 8/1989 | Machida et al. | 424/426 |
| 4,937,254 | 6/1990 | Sheffield et al. | 424/497 |
| 4,946,870 | 8/1990 | Partain, III et al. | 514/777 |
| 4,957,744 | 9/1990 | della Valle et al. | 424/401 |
| 4,965,353 | 10/1990 | della Valle et al. | 536/55.1 |
| 4,970,298 | 11/1990 | Silver et al. | 530/356 |
| 5,095,037 | 3/1992 | Iwamitsu et al. | 514/561 |
| 5,166,331 | 11/1992 | della Valle et al. | 536/55.1 |
| 5,442,053 | 8/1995 | della Valle et al. | 536/55.1 |
| 5,516,765 | 5/1996 | Andermann | 514/57 |

FOREIGN PATENT DOCUMENTS

| | | |
|---|---|---|
| 30806/84 | 7/1984 | Australia . |
| B-72117/87 | 12/1987 | Australia . |
| B-17459/88 | 12/1988 | Australia . |
| B17459/88 | 12/1988 | Australia . |
| B14534/88 | 11/1990 | Australia . |
| 1205031 | 5/1986 | Canada . |
| 1240929 | 8/1988 | Canada . |
| 2031880 | 12/1990 | Canada . |
| 0 312 208 | of 0000 | European Pat. Off. . |
| 0 138 572 | 4/1985 | European Pat. Off. . |
| 0 179 442 | 4/1986 | European Pat. Off. . |
| 0 197 718 | 10/1986 | European Pat. Off. . |
| 0 208 623 | 1/1987 | European Pat. Off. . |
| 0 216 453 | 4/1987 | European Pat. Off. . |
| 0 244 718 | 4/1987 | European Pat. Off. . |
| 0 224 987 | 6/1987 | European Pat. Off. . |
| 0 240 098 | 10/1987 | European Pat. Off. . |
| 0 265 116 | 4/1988 | European Pat. Off. . |
| 0 270 317 | 6/1988 | European Pat. Off. . |
| 0 285 357 | 10/1988 | European Pat. Off. . |
| 0 287 210 | 10/1988 | European Pat. Off. . |
| 0 295 092 | 12/1988 | European Pat. Off. . |
| 0 296 740 | 12/1988 | European Pat. Off. . |
| 0 341 745 | 5/1989 | European Pat. Off. . |
| 0378852 | 12/1989 | European Pat. Off. . |
| 0 378 852 | 7/1990 | European Pat. Off. . |

(List continued on next page.)

OTHER PUBLICATIONS

Sandra Blakeslee, "Solid cores of tumors keeping out best drugs", Jul. 8, 1989, edition of the Globe and Mail, Toronto, Ontario, p. D4.

Pam Harrison, "Toxic drug tamed but still potent", *Ontario Medicine*, vol. 8, No. 16 dated Aug. 21, 1989, p. 1.

*The Merck Index* Eleventh Edition, Centennial Edition, Hyaluronic Acid formulation, pp. 751 and 752.

Alan R. Liss, Inc., Modulation of Immunity in Cancer Patients by Prostaglandin Antagonists, *Immunity to Cancer II* (will follow).

Goodwin, J.S. Prostaglandin E and Cancer Growth Potential for Immunotherapy with Prostaglandin Synthesis Inhibitors, *Augmentive Agents in Cancer Therapy*, Raven Press, New York, (1981) (will follow).

Dr. Samuel Asculai, "Inactivation of Herpes Simplex Viruses by Nonionic Surfactants", *Antimicrobial Agents and Chemotherapy*, Apr. 1978, pp. 686–690 (will follow).

(List continued on next page.)

*Primary Examiner*—Elli Peselev
*Attorney, Agent, or Firm*—Ivor M. Hughes; Neil H. Hughes; Marcelo K. Sarkis

[57] ABSTRACT

A method of treating a disease or condition in a human treatable by a medicine and/or therapeutic agent which may be transported by an agent to the site in need of treatment in the body and which agent may also transport the medicine and/or therapeutic agent to the liver (by for example, the transport agent binding to receptors on the liver) is provided comprising:

(a) administering an effective non-toxic amount of a first agent which does not bind to receptors at the site in need of treatment but which binds with receptors of the liver thereby "down regulating" the liver; and, (b) thereafter administering an effective non-toxic amount of a medicine and/or therapeutic agent and an effective amount of a second agent which is a transport agent and is a different agent from the first agent which binds to the site in need of treatment and would be capable of binding to the sites of the liver if the liver had not been "down regulated" so that its binding capacity for the second agent has been substantially reduced by the up-take by the liver of the first agent administered under sub-paragraph (a) by for example, binding with the scavenger receptors of the liver.

45 Claims, 7 Drawing Sheets

FOREIGN PATENT DOCUMENTS

| | | |
|---|---|---|
| 2364373 | 10/1975 | Germany . |
| 1287041 | of 0000 | Japan . |
| 57-183707 | 11/1982 | Japan . |
| 57-183707 | 12/1982 | Japan . |
| 61-000017 | 1/1986 | Japan . |
| 61-233622 | 10/1986 | Japan . |
| 62-201825 | of 1987 | Japan . |
| 62-201825 | 9/1987 | Japan . |
| 63/045223 | 2/1988 | Japan . |
| A11678/88 | 5/1988 | Japan . |
| 62-287041 | 11/1989 | Japan . |
| 62287041 | 11/1989 | Japan . |
| A-116678/88 | 11/1989 | Japan . |
| 769287 | 3/1957 | United Kingdom . |
| 1283892 | 8/1972 | United Kingdom . |
| 2099826 | 12/1982 | United Kingdom . |
| WO 88/07060 | 9/1988 | WIPO . |
| WO88/07060 | 9/1988 | WIPO . |
| WO89/05645 | 6/1989 | WIPO . |
| WO 89/07932 | 9/1989 | WIPO . |
| WO89/07932 | 9/1989 | WIPO . |
| WO91/04058 | 4/1991 | WIPO . |

OTHER PUBLICATIONS

Alaverdyan MI, Ter–Avetisyan AT. Effect of hyaluronidase, hyaluronic acid, and some other substances on postradiational experimental bacteriemai. *Bulletin of Experimental Biology and Medicine* 1967; 64(9): 967–969.

Balazs EA, Gibbs DA. The rheological properties and biological function of hyaluronic acid. In: *Chemistry and Molecular Biology of the Intercellular Matrix. vol. III.* New York: Academic Press, 1970, pp. 1241–1253.

Balazs EA, Band P. Hyaluronic acid: Its structure and use. *Cosmetics & Toiletries.* Polymers in Cosmetics 1984; 99: 65–72.

Camber O, Lundgren P. Diffusion of some low molecular weight compounds in sodium hyaluronate. *Acta Pharmaceutica Suecica* 1985; 22(6): 315–320.

Camber O, Edman P, Gurny R. Influence of sodium hyaluronate on the meiotic effect of pilocarpine in rabbits. *Current Eye Research* 1987; 6(6): 779–784.

Chang S–C. Pro–drug and vehicle approaches to improve the therapeutic index of topically applied timolol in the pigmented rabbit. *Dissertation Abstracts International* 1988; 49(2): 367–B.

Cravioto, R.O., et al. Effects of Precipitates Formed by Insulin with Hyaluronic Acid and Mucoid From Vitreous Humor in Depressing Blood–Sugar Levels *Science* (1950); vol. 111: 520–521.

Gieldanowski, Jerzy; Skowronska, Jadwiga Studies on immunosuppressive and anti–inflammatory effect of adriamycin. *Arch. Immunol. Ther. Exp.* (1980); 28 (3): 439–446.

Hassan HG, Akerman B, Rank H, Lindberg B, Lindquist B. Effects of adjuvants to local anaesthetics on their duration. *Acta Anaesthesiol. Scand.* 1985; 29: 384–388.

Hurd ER Immunosuppresive and anti–inflammatory properties of cyclophosphamide, azathioprine and methotrexate. *Arthritis and Rheumatism* (1973 Jan.–Feb.); 16 (1): 84–88.

Idson B. Polymers in skin cosmetics. *Cosmetics & Toiletries* 1988; 103: 63–68.

Johansson A, Hassan H, Renck H. Effects of adjuvants to local anaesthetics on their duration. *Acta Anaesthesiol. Scand.* 1985; 29: 736–738.

Kalbhen D.A. The inhibitory effects of steroidal and non–steroidal antirheumatic drugs on articular cartilage in osteoarthrosis and its counteraction by a biological GAG–peptide complex (Rumalon®). *Z. Rheumatol* (1982); 41: 202–211.

Katsu M., Abe T., Shimada S. Significance and clinical use of non–steroid anti–inflammatory drugs as substitutes for steroids in steroid dependence. *Nippon Rinsho* (1968 Jan.); 26(1): 89–95.

Kreis H, Chkoff N, Droz D, et al. Nonsteroid anti–inflammatory agents as a substitute treatment for steroids in ATGAM–treated cadaver kidney recipients. *Transplantation* (1984 Feb.); 37(2): 139–145.

McIlwraith W. Current concepts in equine degenerative joint disease. *Journal of the American Veterinary Medical Association* 1982; Feb. 1: 239–250.

Mizushima, Y. Possibility of non–steroid anti–inflammatory drugs as a substitute for steroid–analysis of the present situation and demands for the future. *Nippon Rinsho* (Jan. 1986); 26(1): 61–65.

Nizolek DJH, White KK. Corticosteroid and hyaluronic acid treatments in equine degenerative joint disease: A review. *The Cornell Veterinarian* 1981; 71(4): 355–375.

Pigman W, et al. Acide hyaluronique et facteurs de preméabilité tissulaire. *Bull. Soc. Chim. Biol.* 1963; 5(2–3): 185–202.

Pruett RC, Schepens CL, Constable IJ, Swann DA. Hyaluronic acid vitreous substitute. In: *Vetreous Surgery and Advances in Fundus Diagnosis and Treatment.* Freeman H.M., et al., Editors. Appleton–Century–Crofts, 1977: Chapter 55, pp. 433–444.

Reim M, Teping C. Surgical procedures in the treatment of most severe eye burns. *Acta Ophthalmologica* 1989–Supplementum 192; 67: 47–54.

Rydell NW, Balazs EA. Effect of intra–articular injection of hyaluronic acid on the clinical symptoms of osteoarthritis and on granulation tissue formation. *Clinical Orthopaedics and Related Research* 1971; 80(Oct.): 25–29.

Saba P, Galeone F, Salvadorini F, Guarguaglini M, Ombrato M. Investigation of the antihyperlipemic activity of an association of clofibrate and extractive mucopolysaccharide complex. *Current Therapeutic Research* 1978; 23(4): 455–463.

Stegman R, Miller D. Use of sodium hyaluronate in severe penetrating ocular trauma. *Acta Ophthalmol.* 1986; 18: 9–13.

Trabucchi E, Foschi D, Marazzi M, Radelli E, Lucianetti A, Rizzitelli E. Baratti C, et al. Prevention of wound dehiscnece in severely obese patients with jejuno–ileal by–pass: The role of hyaluronic acid. *Pharmatherapeutica* 1988; 5(4): 233–239.

Sertoli P, Merello A, Parodi M. L'acido jularonico, per uso topico, nella cura delle ulcere trofocircolatorie degli arti inferiori. (Comunicazioni). *Giornale Itanliano de Dermatologia* 1970; 45(8): 468–471.

Walther, M. The Prevention of Strine Cutis Distansae During Pregnancy. *Mineva Gynecolgia* (1981) vol. 33: 497–499.

Weirich, E.G., Longauer, J.K., Kirkwood, A.H. Dermatopharmacology of salicylic acid. III. Topical contra–inflammatory effect of salicylic acid and other drugs in animal experiments. *Dermatologica* (1976); 152(2): 87–99.

Goodwin, J.S., Prostaglandin E and Cancer Growth: Potential for Immunotherapy with Prostaglandin Synthesis Inhibitors, *Augmetive Agents in Cancer Therapy,* Raven Press, New York (1981), pp. 393–415.

Asculia, Dr. S., "Inactivation of Herpes Simplex Viruses by Nonionic Surfactants", *Antimicobial Agents and Chemotherapy*, Apr. 1978, pp. 686–690.

Sneader, W.E. Chemical Abstracts, vol. 76, No. 10, Possible Mechanism for Action of DMSO on Percutaneous absorption, *J. Pharm. Pharmcol*, 1971, 23 (Supp).

International Preliminary Examination Report for PCT/CA90/00306 and attachement substitute claims.

Alaverdyan et al., "Effect of hyaluronidase, hyaluronic acid, and some other substances on postradiational experimental bacteriemia", *Bulletin of Experimental Biology & Medicine* 1967:64(9):967–969.

Balazs et al, "The rheological properties and biological function of hyaluronic acid", *Chem. and Mol. of the Intracellular Matrix*, vol. 3, 1970, p. 1241–1253.

Balezs E.A. et al, "Hyaluronic acid: Its structure and use", *Cosmetics & Toiletires*, Polymers in Cosmetics 1984; 99: 65–72.

Camber O. et al, "Diffusion of some low molecular weight compounds in sodium hyaluronate", *Acta Pharmaceutica Suecia* 1985; 22(6):315–320.

Camber O. et al, "Influence of sodium hyaluronate on the meiotic effect of pilocarpine in rabbits", *Current Eve Research* 1987: 6(6): 779–784.

Chang S–C, "Prodrug and vehicle approaches to improve the therapeutic index of topically applied timolol in the pigmented rabbit", *Dissertation Abstracts International* 1988; 49(2):367–B.

Cravioto R O et al, Effects of Precipitates Formed by Insulin with Hyaluronic Acid and Mucoid from Vitreous Humor in Depressing Blood–Sugar Levels *Science* (1950); vol. 111:520–521.

Gieldanowski J et al, "Studies on immunosuppressive and anti–inflammatory effects of adriamycin", *Arch. Immunol. Ther. Exp.* (1980); 28(3): 439–446.

Hassan, H.G., et al., "Effects of adjuvants to local anaesthetics on their duration", *Acta Anaesthesiol Scand* 1985; 29: 384–388.

Hurd, E.R., "Immunosuppresive and antiinflammatory properties of cyclophosphamide, azathioprine and methotrexate", *Arthritis and Rheumatism* (1973 Jan./Feb.); 16(1): 84–88.

Idson B, "Polymers in skin cosmetics", *Cosmetics & Toiletries* 1988; 103: 63–68.

Johansson A. et al, "Effects of adjuvants to local anaesthetics on their duration", *Acta Anaesthesiol Scand* 1985; 29: 736–738.

Kalbhen D.A., "The inhibitory effects of steroidal and non–steroidal antirheumatic drugs on articular cartilage in osteoarthrosis and its counteraction by a biological GAG–peptide complex (Rumalon®)", *Z. Rheumatol* (1982): 41: 202–211.

Katsu M. et al., "Significance and clinical use of non–steroid anti–inflammatory drugs as substitutes for steroids in steroid dependence", *Nippon Rinsho* (1986 Jan) 26(1): 89–95.

Kreis H et al, "Nonsteroid antiinflammatory agents as a substitute treatment for steroids in ATGAM–treated cadaver kidney recipients" *Transplantation* (1984 Feb); 37(2): 139–145.

McIlwraith W, "Current concepts in equine degenerative joint disease", *Journal of the Am. Veterinary Medical Assoc*, 1982; Feb. 1, vol. 180: 239–250.

Mizushima Y., "Possibility of non–steroid anti–inflammatory drugs as a substitute for steroids–analysis of the present situtation and demands for the future", *Nippon Rinsho* (Jan. 1986); 26(1): 61–65.

Nizolek D.J.H. et al, "Corticosteroid and hyaluronic acid treatments in equine degerenative joint disease: A Review" *The Cornell Veterinarian* 1981: 71(4): 355–375.

Pigman W et al, "Acide hyaluronique et facteurs de permeabilite tissulaire" *Bull. Soc. Chim. Biol.* 1963; 45(2–3): 185–202.

Pruett RC, et al, "Hyaluronic acid vitreious substitute", In: *Vitreous Surgery and Advances in Fundus Diagnosis and Treatment*, H. McKenzie Freeman et al Editors, Appleton–Century–Crofts, 1977: Chapter 55, pp. 433–444.

Reim M et al, "Surgical procedures in the treatment of most severe eye burns" *Acta Ophthalmologica* 1989–Supplementum 192; 67: 47–54.

Rydell N et al, "Effect of intra–articular injection of hyaluronic acid on the clinical symptoms of osteoarthritis and on gradulation tissue formation" *Clinical Orthopaedics and Related Research* 1971; 80 (Oct.): 25–29.

Saba P et al, "Investigation of antihyperlipemic activity of an association of clofibrate and extractive mucopolysaccharide complex", *Current Therapeutic Research* 1978; 23(4): 455–463.

Stegmann R et al, "Use of sodium hyaluronate in sever penetrating ocular trauma" *Acta Opthalmol.* 1986; 18: 9–13.

Trabucchi E et al, "Prevention of wound dehiscense in severely obese patients with jejuno–ileal by–pass: the role of hyaluronic acid" *Pharmatherapeutica* 1988; 5(4): 233–239.

Sertoli P et al., L'acido jaluronico, per uso topico, nella cura della ulcere trofocirolatorie degli arti inferiori (Comunicazioni) *Giornale Italiano di Dermatologia* 1970; 45(8): 468–471.

Walther M, "The Prevention of Strine Cutis Distansae During Pregnancy", *Minerva Ginecologica* (1981) vol. 33: 497–499.

Weirich E G et al, "Dermatopharmacology of salicyclic acid. III. Topical contra–inflammatory effects of salicylic acid and other drugs in animal experiments", *Dermatologica* (1976); 152(2):87–99.

7 mg CS FOLLOWED BY $^{125}$I-HA

TARGETING OF DOSAGES OF MEDICINE AND THERAPEUTIC AGENTS

This Application is a Continuation-In-Part Application of U.S. applications Ser. No. 07/675,908 filed Jul. 3, 1991, Ser. No. 08/468,328 filed Jun. 6, 1995 and Ser. No. 08/520,591 filed Aug. 30, 1995, the contents of which three applications are incorporated herein by reference.

FIELD OF THE INVENTION

This invention relates to the targeting of medicines and therapeutic agents to sites in the body of a mammal in need of treatment and, in one application, finds use in the treatment of malignant tumours in humans.

BACKGROUND OF THE INVENTION

U.S. application Ser. No. 07/675,908 (from which this Application is a Continuation-In-Part Application) owned by Hyal Pharmaceutical Corporation and PCT Application PCT/CA90/00306, Publication No. WO91 /04058 (from which the above U.S. application Ser. No. 07/675,908 entered the National Phase) also owned by Hyal Pharmaceutical Corporation teaches the use of dosages of at least 10 mg. of forms of hyaluronic acid to transport effective amounts of medicines and/or therapeutic agents to sites in need of treatment in the human body, to penetrate the tissue at the sites in need of treatment, including scar tissue, through all membranes into the cells to be treated.

At page 25, line 17, the PCT Application teaches the additional benefit of using at least about 200 mg. of forms of hyaluronic acid (for example, sodium hyaluronate) in a dosage together with the medicine and/or therapeutic agent for reducing the side effects of the medicine and/or therapeutic agent when administered (such as gastro-intestinal distress, neurological abnormalities, depression, etc. normally associated with the medicine and/or therapeutic agent) even at elevated amounts greater than the usual accepted dosage amounts of the medicine and/or therapeutic agent when administered alone for example, an NSAID (non-steroidal anti-inflammatory agent).

The document continues at page 25, line 26:

"In addition, the responses that have been observed are superior when the NSAID (for example, Indocid™) is combined with hyaluronic acid demonstrating clearly that the combination is now "targeting" the pathological tissue even when administered by the systemic intravenous route. Thus, it has been observed that patients with neoplastic diseases when receiving in addition to other chemicals (for example, ascorbic acid [Vitamin C], phloretin and anti-cancer drugs), 50–200 mg NSAID—hyaluronic acid (sodium hyaluronate) (for example indomethacin and hyaluronic acid) experience dramatic relief of pain immediately. This is followed within a short period of time by a resolution and resorbtion of neoplastic lesions with an improvement of pulmonary, and liver function if there is tumor present in these organs. Thus, the dead tumor material and the debris and tumor toxins appear to be better eliminated by the body through the action of the macrophages whose activity is enhanced by the addition of the NSAID (or a steroidal anti-inflammatory drug) administered with hyaluronic acid (or salt or other form thereof). Thus Applicants believe that the addition of the NSAID for example with hyaluronic acid (sodium hyaluronate) deblocks the macrophages by preventing enzymatic production of prostaglandin synthetase which blocks macrophage functioning. Thus the hyaluronic acid (and salt and other forms) not only enhance the activity of the NSAID but also reduce any side effects and toxicity that is associated with the use of the prostaglandin synthesis inhibitors."

U.S. application Ser. Nos. 08/486,328 and 08/520,591 and PCT Application PCT/CA95/00477, also owned by Hyal Pharmaceutical Corporation, teach the modulation of cellular activity of tissue and cells expressing a high affinity cell-surface receptor for hyaluronic acid by the use of forms of hyaluronic acid. These cell surface receptors comprise adhesion molecule ICAM-1, adhesion molecule CD44 and adhesion molecule HARLEC (Hyaluronic Acid [Hyaluronan] Receptors Liver Endothelial Cells) and regulatory molecule RHAMM (Receptor for HA Mediated Motility), for binding hyaluronan. HARLEC is expressed (produced and put on the cell surface) in liver endothelial cells. The administration of an effective amount of a form of hyaluronic acid to bind with the cell-surface receptors modulates cellular activity of tissues and/or cells expressing such high affinity cell-surface receptors for hyaluronic acid (for example, an adhesion or regulatory molecule) in the human body.

As stated at page 19, line 30 of the Application, the binding capacity of the liver has been found to be so great for hyaluronan that hyaluronan when administered first goes to the liver and if not bound to the liver because the liver has reached its binding capacity for hyaluronan, circulates in the system and collects in for example, a tumour because of the tumour's receptors' ability to bind with hyaluronic acid (hyaluronan) as a result of the tumour having excess receptors for hyaluronic acid (more than normal tissue and cells).

Therefore, if hyaluronic acid is used as a vehicle for a medicine or therapeutic agent to transport the medicine to a site in the body in need of treatment, unless the combination is administered directly to the site in need of treatment as by injection into a tumour, much of the combination ends up at the liver with lesser amounts at the site in need of treatment, unless and until the liver has reached its binding capacity for hyaluronan.

In an article entitled "Binding of hyaluronate and chondroitin sulphate to liver endothelial cells" by Tovard C. Laurent, et al., Biochem J. (1986) 234, 653–658, the authors discussed the fact that "Circulating sodium hyaluronate (HA) is efficiently taken up and metabolized by the endothelial cells in the liver sinusoids", and that "Chondroitin sulphate (CSA) is also taken up and metabolized by liver endothelial cells". The authors also state:

"The partial inhibition of HA binding by CSA (Smedared et al., 1984) and the inhibition of CSA binding by HA (Smedared et al., 1985) indicates that the two polysaccharides are recognized by the same receptor. We have now confirmed this hypothesis by the use of oligosaccharides of identical degree of polymerization prepared from the two polymers."

I have now discovered that the liver endothelial cells carry at least two different binding proteins for HA (hyaluronan) including a scavenger receptor that binds to both chondroitin sulphate and hyaluronan, (and other glycosaminoglycan (GAGS)) and, the majority of these different binding proteins (the scavenger receptors on the liver) are inhibited from their take-up of GAGS (Glycosaminoglycans) including chondroitin sulphate (CS) by their being previously bound to, for example, chondroitin sulphate. I have also discovered that the sites in need of treatment for example, metastatic tumours do not carry the same scavenger receptors that bind to chondroitin sulphate. These sites carry receptors that do bind to hyaluronan. Thus, by first administering for example, chondroitin sulphate for take up by the scavenger receptors of the liver, subsequently administered hyaluronan for example, will not be taken by the liver.

It is therefore an object of this invention to provide a novel method of treatment of a disease or condition in a human which method permits substantially more of the medicine and/or therapeutic agent to be brought to the site in the body in need of treatment.

It is a further object of the invention to target sites in the body in need of treatment so that any medicine or therapeutic agent reaches the site in need of treatment rather than being taken up elsewhere in the body (for example, the liver).

It is still a further object of the invention to provide a novel dosage kit or combination of materials or chemicals which when used one after the other will target the sites in the body in need of treatment for delivery of a medicine and/or therapeutic agent to the site in need of treatment.

It is still a further object of the invention to reduce the amount of the medicine and/or therapeutic agent that would otherwise be normally expected to be used for treating a disease or condition. In this regard, if a transport agent is used to transport the medicine and/or therapeutic agent to the site of the disease and/or condition, it is a further object of the invention to use less of the usual amount of the transport agent (for example, hyaluronan and a pharmaceutically acceptable salt thereof) for transporting the medicine and/or therapeutic agent to transport the medicine and/or therapeutic agent to the site of the treatment. Thus, for example, less cytotoxic medicine (for example, methotrexate, cisplatin and the like) will be needed as an effective dosage amount of the medicine to achieve successful treatment using less than the usual effective dosage amount of the hyaluronan for example, as the transport agent.

Further and other objects of the invention will be realized by those skilled in the art from the following Summary of Invention and Detailed Description of Examples thereof.

SUMMARY OF INVENTION

I have now discovered that while chondroitin sulphate and hyaluronan bind to liver cells and particularly, the scavenger receptors on the liver, chondroitin sulphate does not bind with the receptors on for example, tumours (for example, metastatic tumours) and particularly, the cell surface receptors for hyaluronan comprising, the Regulatory molecule RHAMM (Receptor for HA Mediated Motility), and adhesion molecules ICAM-1, HARLEC and CD44. This has led me to develop my new methods of treatment of disease and conditions including metastatic tumours. By "down regulating" the scavenger receptors on the liver cells by binding them to administered chondroitin sulphate (or other GAGS [Glycosaminoglycan] such as dextran sulphate, other than a form of hyaluronan) and subsequently administering the form of hyaluronic acid (hyaluronan) with the medicine and/or therapeutic agent, the subsequently administered amounts of hyaluronan (which transport the medicine and/or therapeutic agent) are picked up, not by the liver whose binding capacity has been substantially fulfilled but, by other sites capable of binding with forms of hyaluronan having excess unfilled hyaluronan receptors (such as on metastatic tumours). At the same time, the hyaluronan transports any medicine (or therapeutic agent) to treat the sites in need of treatment (for example, by an effective amount of a cytotoxic agent to treat a tumour). As a result, I have, by the pre-treatment with for example, chondroitin sulphate, found that less of the form of the transport agent for example, hyaluronan that is to be subsequently administered is required than previously used. I have also found that less of the medicine and/or therapeutic agent is required than was used previously to provide a successful treatment of the disease and/or condition.

The amount of the chondroitin sulphate that will "down regulate" the liver cells is preferably in the order of at least about 3–5 mg. of chondroitin sulphate per kilogram of body weight of the patient. However, preferably greater amounts (mg/kg) are administered to "turn off" the liver. Because the liver processes the administered and "taken up" chondroitin sulphate rapidly, less chondroitin sulphate is not as good as more, as after several hours the liver has processed all the chondroitin sulphate. Thus, prolonged "blockage"/"down regulating" or "immobilization" of the liver cells is preferred. Where chondroitin sulphate (equivalent dose 1–2 grams/70 kg person) is administered, the take-up of even small amounts of hyaluronan by the liver (0.5–1 mg/70 kg/person) can be inhibited for an extended time by the administration of the chondroitin sulphate. Thus, the hyaluronan is available to transport the medicine and/or therapeutic agent to the site in need of treatment (for example, methotrexate or cisplatin to a tumour or furosemide to a kidney or other use proposed by the teachings of WO 91/04058 which is incorporated herein by reference.

The amount thereafter required of the transport agent for example, hyaluronan or a pharmaceutically acceptable salt thereof for example, sodium hyaluronate having for example, a molecular weight less than 750,000 daltons may be reduced substantially (for example, to an amount of substantially less than 10 mg/70 kg person such as 0.1 mg/70 kg person) and the amount of medicine and/or therapeutic agent likewise substantially reduced to a mere fraction of what is normally used previously or proposed to be used previously. It may be that with the liver shut down, only micrograms ($\mu$g)/kg of the body weight, of the transport agent for example, 20 $\mu$g/kg and micrograms ($\mu$g) of the medicine for example, depending on the medicine 10 $\mu$g/kg of body weight may be only required in the dosage.

Other suitable compounds may be substituted for chondroitin sulphate such as dextran sulphate including other GAGS. Some may be used in substantially the same amounts as with chondroitin sulphate; others may be used in higher or lower amounts. Other GAGS may include Dermatan sulphate, Heparin sulphate, Heparin or their Proteoglycan forms, Keratan sulphate. Keratan sulphate and the like, while not technically a glycosaminoglycuronoglycan, will be considered to be included as a GAG herein. Other scavenger receptor ligands may also be used such as acetylated low density lipoproteins (LDL), acids such as polyinosinic acid and the like.

Subsequent to administering the chondroitin sulphate (for example, after 3 to 4 minutes) (for example, by intravenous administration) the combination of for example, hyaluronan (for example, the amounts, forms and molecular weights taught in U.S. application Ser. No. 07/675,908 and PCT Application WO91/04058 and Continuation-In-Part application Ser. No. 08/468,328 filed Jun. 6, 1995 and Ser. No. 08/520,591 filed Aug. 30, 1995 (the contents of all four of which are incorporated herein by reference), together with the medicine and/or therapeutic agent (whether excess amounts over and above the normally administered amounts when at least 200 mg/70 kg person of the form of hyaluronic acid is used or the normally used effective amounts of the medicine or therapeutic agents are used or much lesser amounts ($\mu$g)/kg) is administered by any suitable means.

Because lesser amounts of medicine and/or therapeutic agents and for example, hyaluronan may now be used, the amounts specified above and in the documents which are incorporated herein by reference may be substantially reduced. Because the amount of medicine and/or therapeutic agent is reduced substantially, side effects are substantially reduced. Thus, even the 200 mg. amount per 70 kg. person of the form of hyaluronic acid will be reduced. In fact, with the liver being "blocked", I have found that 5 μg/250 mg rat (20 μg/1 kg) of hyaluronan targets the site in need of treatment. I have also found that the same order of magnitude (μg/250 gm rat) medicine and/or therapeutic agent in the dosage would be useful for treatment of the site in need of treatment. That is because the liver has now been "blocked". Therefore, the teachings in WO 91/04058 with respect to dosage amounts may now be modified in light of the above for use with this invention.

As stated in Application WO91/04058, whose teachings are incorporated herein by reference:

(i) at page 17, line 3 to page 18, line 16:

"Applicants have now discovered that combinations and formulations (for example an injectable formulation) can be provided for administration to a mammal for the treatment of a disease or condition, which combinations or formulations employ or incorporate as the case may be a therapeutically effective non-toxic amount of a medicinal and/or therapeutic agent to treat the disease or condition (for example a free radical scavenger (for example ascorbic acid (Vitamin C)), Vitamin C (for the treatment of mononucleosis), an anti-cancer agent, chemotherapeutic agent, anti-viral agents for example a nonionic surfactant, e.g. nonoxynol-9 [nonylphenoxy polyethoxy ethanol] found in Delfen™ contraceptive cream, and anionic surfactants (e.g. cetyl pyridinium chloride) and cationic surfactants (e.g. benzalkonium chloride), non-steroidal anti-inflammatory drugs (NSAID) for example indomethacin, naproxen and (+/−) tromethamine salt of ketorolac (sold under the trademark ToradoliJ) and steroidal anti-inflammatory drugs, anti-fungal agent, detoxifying agents (for example for administration rectally in an enema), analgesic, bronchodilator, anti-bacterial agent, antibiotics, drugs for the treatment of vascular ischemia (for example diabetes and Berger's disease), anti-body monoclonal agent, minoxidil for topical application for hair growth, diuretics (for example furosemide (sold under the trademark LasixJ)), immunosuppressants (for example cyclosporins), lymphokynes (such as interleukin-2 and the like), alpha-and-β-interferon and the like) administered with, or carried in, an amount of hyaluronic acid and/or salts thereof (for example the sodium salt) and/or homologues, analogues, derivatives, complexes, esters, fragments, and/or sub units of hyaluronic acid (preferably hyaluronic acid and salts thereof) sufficient to facilitate the agent's penetration through the tissue (including scar tissue), at the site to be treated through the cell membranes into the individual cells to be treated. When such combinations and formulations are administered to patients suffering from the disease or condition, the disease or condition is unexpectedly improved.

The formulation can be administered among other methods, intravenously, intra arterially, intraperitoneally, intrapleurally, transdermally, on the skin (topically), rectally, orally or by direct injection (for example into a tumor, into an abscess or similar disease focus) or put on a patch to be secured to the skin of the patient. The hyaluronic acid and/or salts thereof and the agent can be administered separately but are administered in sufficient amounts and in an immediate time sequence or interval (preferably concurrently and more preferably simultaneously), preferably at the identical site (e.g. one given intravenously and the other "piggy backed"), to treat the disease or condition."

(ii) at page 25, line 18 to page 26, line 14:

"Thus and according to another aspect of the invention when an NSAID for example indomethacin (dissolved in n-methyl glucamine) or other NSAID is administered with greater than 200 mg hyaluronic acid for 1–2 mg/kg body weight of the NSAID (in one instance indomethacin and NMG), no major toxic side effects occur such as gastro-intestinal distress, neurological abnormalities, depression, etc., even at elevated amounts of indomethacin (if necessary). If the amount of hyaluronic acid is decreased below that amount, the usual side effects may begin to reoccur. In addition, the responses that have been observed are superior when the NSAID (for example IndocidJ) is combined with hyaluronic acid demonstrating clearly that the combination is now "targeting" to the pathological tissue even when administered by the systemic intravenous route. Thus, it has been observed that patients with neoplastic diseases when receiving in addition to other chemicals (for example ascorbic acid [Vitamin C], phloretin and anti-cancer drugs), 50–200 mg NSAID-hyaluronic acid (sodium hyaluronate) (for example indomethacin and hyaluronic acid) experience dramatic relief of pain immediately. This is followed within a short period of time by a resolution and resorbtion of neoplastic lesions with an improvement of pulmonary, and liver function if there is tumor present in these organs. Thus the dead tumor material and the debris and tumor toxins appear to be better eliminated by the body through the action of the macrophages whose activity is enhanced by the addition of the NSAID (or a steroidal anti-inflammatory drug) administered with hyaluronic acid (or salt or other form thereof). Thus Applicants believe that the addition of the NSAID for example with hyaluronic acid (sodium hyaluronate) deblocks the macrophages by preventing enzymatic production of prostaglandin synthetase which blocks macrophage functioning. Thus the hyaluronic acid (and salt and other forms) not only enhance the activity of the NSAID but also reduce any side effects and toxicity that is associated with the use of the prostaglandin synthesis inhibitors.

Examples of agents suitable for use as chemotherapeutic agents are novantrone (Mitoxantrone), Methotrexate, 5-FU (5-Fluouracil), carboplatinum, methyl CCNU administered orally and Mitomycin C."

(iii) at page 26, lines 32 to 37:

"The hyaluronic acid and salts thereof may be utilized at varying doses −10 to 1000 mg/70 kg person with the optimal doses tending to range between 50 and 350 mg/70 kg individual. As there is no toxicity, the hyaluronic acid can obviously be administered in a dose excess (for example 3000 mg/70 kg individual) without any adverse effects."

(iv) at page 29, line 27 to page 33, line 31:

"One form of hyaluronic acid and/or salts thereof (for example sodium salt) and homologues, analogues, derivatives, complexes, esters, fragments, and sub units of hyaluronic acid, preferably hyaluronic acid and salts and thereof suitable for use with Applicant's invention is a fraction supplied by Sterivet Laboratories Limited. One such fraction is a 15 ml vial of Sodium hyaluronate 20 mg/ml (300 mg/vial—Lot 2F3). The sodium hyaluronate fraction is a 2% solution with a mean average molecular weight of about 225,000. The fraction also contains water q.s. which is triple distilled and sterile in accordance with the U.S.P. for injection formulations. The vials of hyaluronic acid and/or salts thereof may be carried in a Type 1 borosilicate glass vial closed by a butyl stopper which does not react with the contents of the vial."

The fraction of hyaluronic acid and/or salts thereof (for example sodium salt) and homologues, analogues, derivatives, complexes, esters, fragments, and sub units of hyaluronic acid, preferably hyaluronic acid and salts thereof may comprise hyaluronic acid and/or salts thereof having the following characteristics:

a purified, substantially pyrogen-free fraction of hyaluronic acid obtained from a natural source having at least one characteristic selected from the group consisting of the following:

i) a molecular weight within the range of 150,000–225,000;
ii) less than about 1.25% sulphated mucopolysaccharides on a total weight basis;
iii) less than about 0.6% protein on a total weight basis;
iv) less than about 150 ppm iron on a total weight basis;
v) less than about 15 ppm lead on a total weight basis;
vi) less than 0.0025% glucosamine;
vii) less than 0.025% glucuronic acid;
viii) less than 0.025% N-acetylglucosamine;
ix) less than 0.0025% amino acids;
x) a UV extinction coefficient at 257 nm of less than about 0.275;
xi) a UV extinction coefficient at 280 nm of less than about 0.25; and
xii) a pH within the range of 7.3–7.9. Preferably the hyaluronic acid is mixed with water and the fraction of hyaluronic acid fraction has a mean average molecular weight within the range of 150,000–225,000. More preferably the fraction of hyaluronic acid comprises at least one characteristic selected from the group consisting of the following characteristics:

i) less than about 1% sulphated mucopolysaccharides on a total weight basis;
ii) less than about 0.4% protein on a total weight basis;
iii) less than about 100 ppm iron on a total weight basis;
iv) less than about 10 ppm lead on a total weight basis;
v) less than 0.00166% glucosamine;
vi) less than 0.0166% glucuronic acid;
vii) less than 0.0166% N-acetylglucosamine;
viii) less than 0.00166% amino acids;
x) a UV extinction coefficient at 257 nm of less than about 0.23;
xi) a UV extinction coefficient at 280 nm of less than 0.19; and
xii) a pH within the range of 7.5–7.7.

Other forms of hyaluronic acid and/or its salts, and homologues, derivatives, complexes, esters, fragments and sub units of hyaluronic acid may be chosen from other suppliers, for example those described in the prior art documents previously referred to. In addition Applicants have successfully employed sodium hyaluronate produced and supplied by LifeCore J Biomedical, Inc. having the following specifications

| Characteristics | Specification |
|---|---|
| Appearance | White to cream colored particles |
| Odor | No perceptible odor |
| Viscosity Average Molecular Weight | <750,000 Daltons |
| UV/Vis Scan, 190–820 nm | Matches reference scan |
| OD, 260 nm | <0.25 OD units |
| Hyaluronidase Sensitivity | Positive response |
| IR Scan | Matches reference |
| pH, 10 mg/g solution | 6.2–7.8 |
| Water | 8% maximum |
| Protein | <0.3 mcg/mg NaHy |
| Acetate | <10.0 mcg/mg NaHy |

| Heavy Metals, maximum ppm | | | | | | | | |
|---|---|---|---|---|---|---|---|---|
| As | Cd | Cr | Co | Cu | Fe | Pb | Hg | Ni |
| 2.0 | 5.0 | 5.0 | 10.0 | 10.0 | 25.0 | 10.0 | 10.0 | 5.0 |

| | |
|---|---|
| Microbial Bioburden | None observed |
| Endotoxin | <0.07 EU/mg NaHy |
| Biological Safety Testing | Passes Rabbit Ocular Toxicity Test |

The following references teach hyaluronic acid, sources thereof and processes of the manufacture and recovery thereof.

U.S. Pat. No. 4,141,973 teaches hyaluronic acid fractions (including sodium salts) having:

(a) an average molecular weight greater than about 750,000, preferably greater than about 1,200,000—that is, a limiting viscosity number greater than about 1400 $cm^3/g.$, and preferably greater than about 2000 $cm^3/g.$;
(b) a protein content of less than 0.5% by weight;
(c) ultraviolet light absorbance of a 1% solution of sodium hyaluronate of less than 3.0 at 257 nanometers wavelength and less than 2.0 at 280 nanometers wavelength;
(d) a kinematic viscosity of a 1% solution of sodium hyaluronate in physiological buffer greater than about 1000 centistokes, preferably greater than 10,000 centistokes;
(e) a molar optical rotation of a 0.1–0.2% sodium hyaluronate solution in physiological buffer of less than $-11 \times 10^3$ degree—$cm^2$/mole (of disaccharide) measured at 220 nanometers;
(f) no significant cellular infiltration of the vitreous and anterior chamber, no flare in the aqueous humor, no haze or flare in the vitreous and no pathological changes to the cornea, lens, iris, retina, and choroid of the owl monkey eye when one milliliter of a 1% solution of sodium hyaluronate dissolved in physiological buffer is implanted in the vitreous replacing approximately one-half the existing liquid vitreous, said HUA being
(g) sterile and pyrogen free and
(h) non-antigenic.

Canadian Letters Patent 1,205,031 (which refers to U.S. Pat. No. 4,141,973 as prior art) refers to hyaluronic acid fractions having average molecular weights of from 50,000 to 100,000; 250,000 to 350,000; and 500,000 to 730,000 and discusses processes of their manufacture.

Where high molecular weight hyaluronic acid (or salts or other forms thereof) is used, it must be diluted to permit administration and ensure no intramuscular coagulation."

(v) and, at page 33, line 37 to page 35, line 30:

"Thus Applicant has combined hyaluronic acid (and sodium hyaluronate and/or other forms) with medicinal and/or therapeutic agents for the treatment of conditions and diseases with totally unexpected results:

For Example

| Condition/Disease | Chemicals & Drugs |
|---|---|
| 1. Cancer, increasing activity of macrophages | free radical scavenger, superoxide dismutase, ascorbic acid (Vitamin C) anti-cancer drugs, NSAID, Chemotherapeutic Agents, detoxifying Agents (e.g. cholestyramine) |
| 1A. Reduction of swelling in brain of (DMSO) person suffering brain trauma | Dimethyl Sulfoxide |
| 2. Hair growth grow more hair when applied topically | minoxidil-combination- |
| 3. Herpes, canker sore, shingles | nonionic surfactants, e.g., nonoxynol-9 and anionic, (e.g. cetyl pyridinium chloride) and cationic (e.g. benzalkonium chloride), surfactants |
| 4. Renal failure, cardiac insufficiency, hypertension, edema | diuretics-furosemide |
| 5. Infection, acne, mononucleosis | antibiotics, antibacterials, antimicrobial, etc., ascorbic acid and hyaluronic acid |
| 6. Transplants | cyclosporins |
| 7. Inflammation, elimination of tumor break down material (toxins and debris), decreasing side effects, relief of pain (e.g. back pain) | non-steroidal anti-inflammatories, NSAID e.g. diclofenac, indomethacin, piroxicam, ibuprofen, tromethamine salt of Ketorolac, naproxen, |
| 8. Detoxification | enema, detoxifying agent, peritoneal dialysis |
| 9. Bronchodilation | bronchodilators, e.g. beclomethasone diproprionate (sodium cromoglycate although not specifically a bronchodialator), theophylline |
| 10. Vascular ischemia | treat limbs in respect of diabetes, Berger's disease, etc. with suitable medicine e.g. Trental |
| 11. HIV (AIDS) | DMSO, Vitamin C, NSAID (e.g. indomethacin, naproxen, ketorolac tromethamine), interferon, VibramycinJ, (doxcycline), tetracycline |
| 12. Diabetes | insulin |
| 13. Post-menopause | estrogens replacement |
| 14. Prevention of topical | antimetabolites (e.g. infection sulfonamides) |
| 15. Reduction of swelling | DMSO |
| 16. Hypertension, cardiac Blockers | Calcium channel blockers e.g. insufficiency-Nifedipine β- e.g. atenolol, propranolol |
| 17. Prostaglandin Synthesis inhibition | acetylsalicylic acid |
| 18. Enhance oxygenation of tissue by perfusion fluid bathing the tissue (for transplantation purposes" | perfusate |

The above description and proposals will apply herein only modified to reflect the benefits of this invention. Thus, the administration of the form of hyaluronic acid and, medicine and/or therapeutic agent described above and identified in the Applications incorporated herein by reference may now be preceded by an effective amount (for example, exceeding in the order of about 3–5 mg/kg of body weight) of chondroitin sulphate (for example, 200–400 mg/70 kg person). As a result, less medicine and/or therapeutic agent for example, a cytotoxic agent, and transport agent for example, hyaluronan, than would be normally or usually used for the treatment, may now be required because the hyaluronan together with the medicine and/or therapeutic agent now goes to the site in need of treatment (tumour, for example) and is not taken up by the liver which has now been "down regulated". Thus, the liver would not be as damaged by the for example, cytotoxic agent as in the past.

The chondroitin sulphate preferably may have a molecular weight exceeding 20,000 daltons for example, in the order of about between 20,000 and 40,000 daltons although there is a benefit irrespective of the molecular weight of chondroitin sulphate administered. Preferably, higher molecular weight chondroitin sulphate is used so long as it is in a dosage form that can be administered effectively (for example, in sufficient sterile water for intravenous purposes). The dextran sulphate or other agents (such as other glycosaminoglycans) may have a molecular weight for example, in the range between about 20,000 and 500,000 daltons or higher provided the dosages can be effectively administered.

Thus, according to one aspect of the invention, a method of treating a disease or condition in a human treatable by a medicine and/or therapeutic agent which may be transported by an agent (for example, a form of hyaluronic acid such as sodium hyaluronate) to the site in need of treatment in the body and which agent may also transport the medicine and/or therapeutic agent to the liver (by for example, the transport agent binding to receptors on the liver) is provided comprising:

(a) administering an effective amount of a first agent such as chondroitin sulphate which does not bind to receptors at the site in need of treatment but which binds with receptors of the liver thereby "down regulating" the liver; and, (b) thereafter (for example, 3 to 4 minutes after the administration under sub-paragraph (a) of this paragraph) administering an effective non-toxic amount of a medicine and/or therapeutic agent and an effective amount of a second agent which is a transport agent [for the medicine and/or therapeutic agent] and is a different agent from the first agent (for example, a form of hyaluronic acid) and which second agent binds to the site in need of treatment and would be capable of binding to the sites of the liver if the liver had not been "down regulated" so that the liver's binding capacity for the second agent has been substantially reduced (preferably substantially eliminated or blocked) by the up-take by the liver of the first agent (for example, chondroitin sulphate Molecular Weight 20,000) administered under sub-paragraph (a) by for example, binding with the scavenger receptors of the liver.

Because the liver has been "down regulated", the amounts of medicine and/or therapeutic agent that may be effective to treat the site in need of treatment is substantially reduced. As well, the amount of the for example, form of hyaluronic acid (transport agent) is substantially reduced so that the effective amount is substantially less than 10 mg/70 kg person (for example, 20 g/kg of body weight of the patient being treated).

According to another aspect of the invention, a method of protecting the liver from taking up medicines and/or therapeutic agents toxic to the liver when administering the medicine and/or therapeutic agent to a site in need of treatment, is provided comprising:

(a) administering an effective amount of a first agent such as chondroitin sulphate which does not bind to receptors at the site in need of treatment but which binds with receptors of the liver thereby "down regulating" the liver; and, (b) thereafter (for example, 3 to 4 minutes after the administration under sub-paragraph (a) of this paragraph) administering an effective non-toxic amount of a medicine and/or therapeutic agent and an effective amount of a second agent which is a transport agent and is a different agent from the first agent, (for example, a form of hyaluronic acid) and which second agent binds to the site in need of treatment and would be capable of binding to the sites of the liver if the liver had not been "down regulated" so that its binding capacity for the second agent has been substantially reduced (preferably substantially eliminated or blocked) by the up-take by the liver of the first agent (for example, chondroitin sulphate, Molecular Weight 20,000) administered under sub-paragraph (a) by for example, binding with the scavenger receptors of the liver.

The amount of the first agent administered under (a) for example, in the order of at least about 3–5 mg/kg of body weight (for example, 200–400 mg/70 kg person) having preferably a molecular weight in the range of 20,000 to 40,000 daltons, may be administered by any suitable manner such as systemically for example, orally, intravenously, subcutaneously or by direct injection proximate, adjacent, or into, the liver (by direct administration into the hepatic artery). Thereafter, (for example, after 3 to 4 minutes) the amount of the second agent for transport in sub-paragraph (b) for example, sodium hyaluronate having a molecular weight less than 750,000 daltons is administered in an effective amount now found to be substantially less than 10 mg/70 kg person discussed in WO 91/04058 together with the medicine and/or therapeutic agent. The at least 200 mg/70 kg person of for example, the sodium hyaluronate provided in Application WO91/04058 to reduce the side effects of the medicine and/or therapeutic agent may now be substantially reduced because the amount of the medicine and/or therapeutic agent that is now effective is substantially less than previously provided. Thus, less of for example, the form of hyaluronic acid may now be administered in a dosage together with a lesser amount of what is now an effective amount of medicine and/or therapeutic agent to reduce the side effects of the medicine and/or therapeutic agent. Thus, the amounts of the medicine and/or therapeutic agent and hyaluronan transport agent may now be (g) microgram amounts per kilogram of body weight to be effective.

The first agent may be chondroitin sulphate (preferably) or other suitable agent (such as dextran sulphate or other GAGS [Glycosaminoglycans] and/or their proteoglycan forms which are not a form of hyaluronic acid). Other scavenger receptor ligands which are effective may also be used as the first agent. The second agent is preferably a form of hyaluronic acid such as hyaluronan or sodium hyaluronate.

Therefore, according to another aspect of the invention, I have provided a dosage kit for maximizing the amount of medicine and/or therapeutic agent to be delivered to a site in the body in need of treatment and/or for protecting the liver from taking up medicine and/or therapeutic agent (particularly cytotoxic agents) when medicines and/or therapeutic agents must be delivered to treat sites other than the liver, comprising:

(a) an effective dosage amount of a first agent such as chondroitin sulphate which does not bind to receptors at the site in need of treatment but which binds with receptors of the liver to thereby "down regulate" the liver;

and, separately from the dosage amount of (a), and, (b) an effective dosage amount comprising an effective non-toxic dosage amount of a medicine and/or therapeutic agent and an effective amount of a second agent which is a transport agent and is a different agent from the first agent (for example, a form of hyaluronic acid) and which second agent will bind to the site in need of treatment and would be capable of binding to the sites of the liver if the liver is not down regulated so that the liver's binding capacity for the second agent has been substantially reduced (preferably eliminated or blocked) by the up-take by the liver of the first agent (for example, chondroitin sulphate Molecular Weight 20,000) when administered after for example, at least about 3–4 minutes after administration of the dosage amount of the first agent under sub-paragraph (a) by for example, binding with the scavenger receptors of the liver.

The dosage amounts for sub-paragraph (b) may be microgram (g) per kilogram of body weight for example, 20 g/kg.

Further, according to another aspect of the invention a method is provided, comprising:

(a) administering an effective amount of a first agent which does not bind to receptors at the site in need of treatment but which binds with receptors of the liver thereby "down regulating" the liver; and, (b) thereafter administering an effective amount of a medicine and/or therapeutic agent (for example, an NSAID [non-steroidal anti-inflammatory agent] or cytotoxic agent (for example, methotrexate and cisplatin and combinations thereof) and an effective amount of a second agent which is a transport agent and is a different agent from the first agent and which second agent is a transport agent which binds to the site in need of treatment and transports to the interstitial fluid, lymph and lymph nodes, and would be capable of binding to the sites of the liver if the liver had not been "down regulated" so that its binding capacity for the second agent has been substantially reduced by the up-take by the liver of the first agent administered under sub-paragraph (a) by binding with the scavenger receptors of the liver.

The first agent may be chondroitin sulphate and the second agent may be a form of hyaluronic acid. The amounts of each may be as previously discussed. For example, the amount of chondroitin sulphate may exceed at least about 3–5 mg/kg and the effective amount of the form of hyaluronic acid may exceed 0.1 mg/70 kg person and may have a molecular weight less than 750,000 daltons.

The invention will now be illustrated by reference to the following Figures and examples and discussion with respect thereto.

Figure 1:
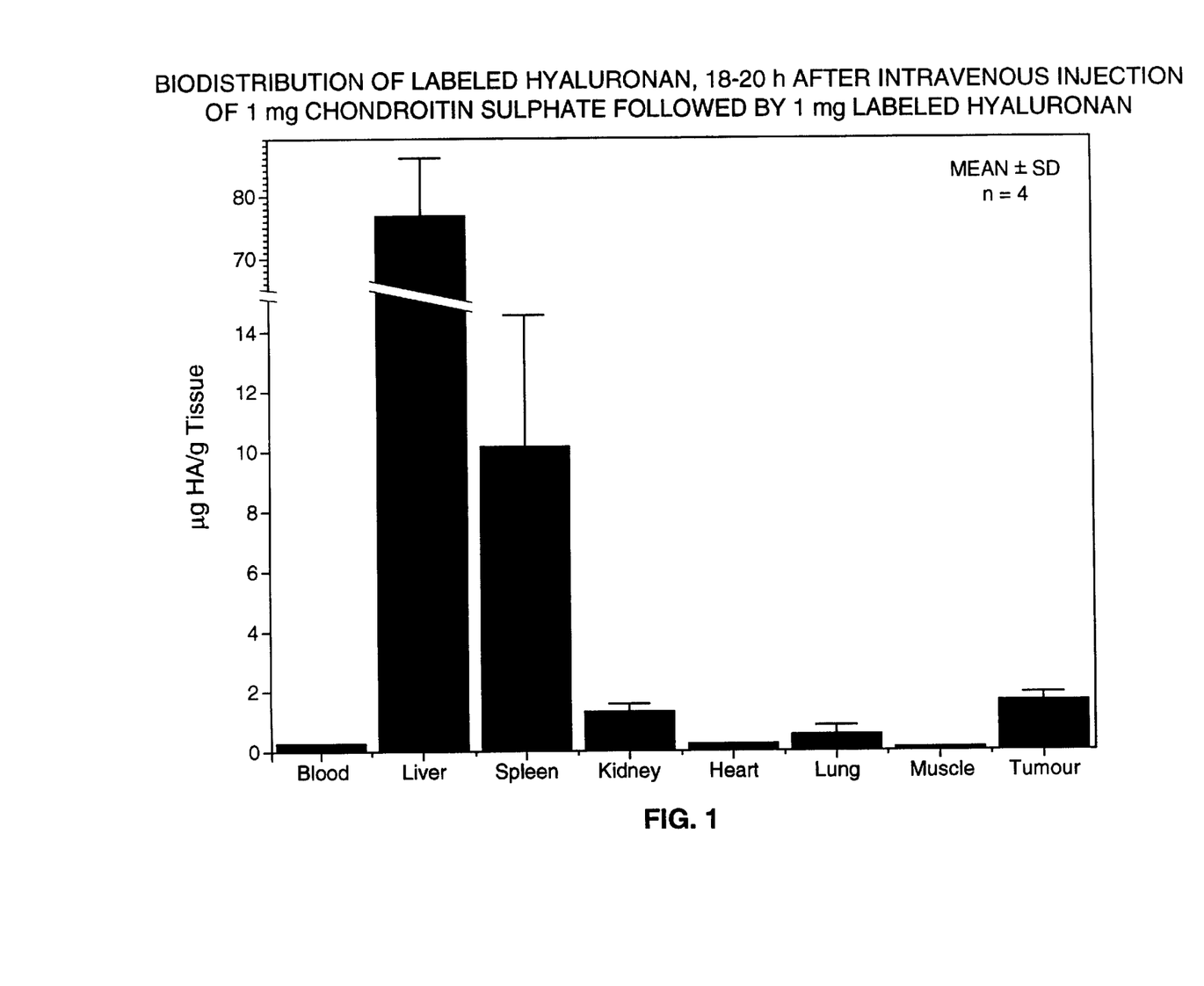
FIG. 1 illustrates the Biodistribution of Labeled Hyaluronan, 18–20 h after Intravenous Injection of 1 mg Chondroitin Sulphate Followed by 1 mg Labeled Hyaluronan.

A summary of the data I have developed on tumour targeting using radiolabelled hyaluronan (HA) administered after chondroitin sulphate (CS) pretreatment is set out in the Figures and is discussed below. I used female Wistar FU rats (weight in the order of 250 gm per rat on average) inoculated in one hind leg with a rat colon carcinoma called NGW to develop the data. When the tumours appeared, the rats received an intravenous injection of 1 mg chondroitin sulphate (200–400 mg/70 kg person) followed 30 seconds later by 1 mg HA (hyaluronan) of low specific radioactivity. 18 to 20 hours later the animals were sacrificed and the radioactivity in the organs measured (see FIG. 1).

I have with the same model used 1 mg HA (hyaluronan) of similar specific activity alone and found a tumour to non-tumour ratio of 7.79+5.00.

Figure 2:
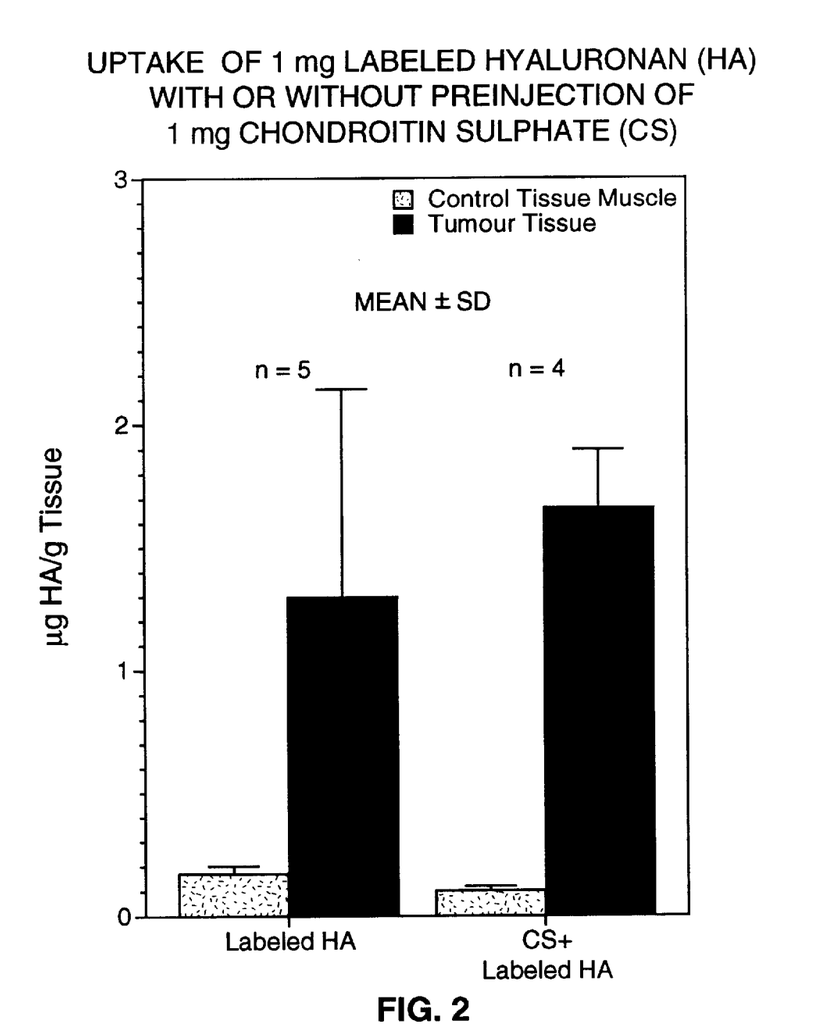
FIG. 2 illustrates the Uptake of 1 mg Labeled Hyaluronan (HA) With or Without Preinjection of 1 mg Chondroitin Sulphate (CS)
Figure 2B:
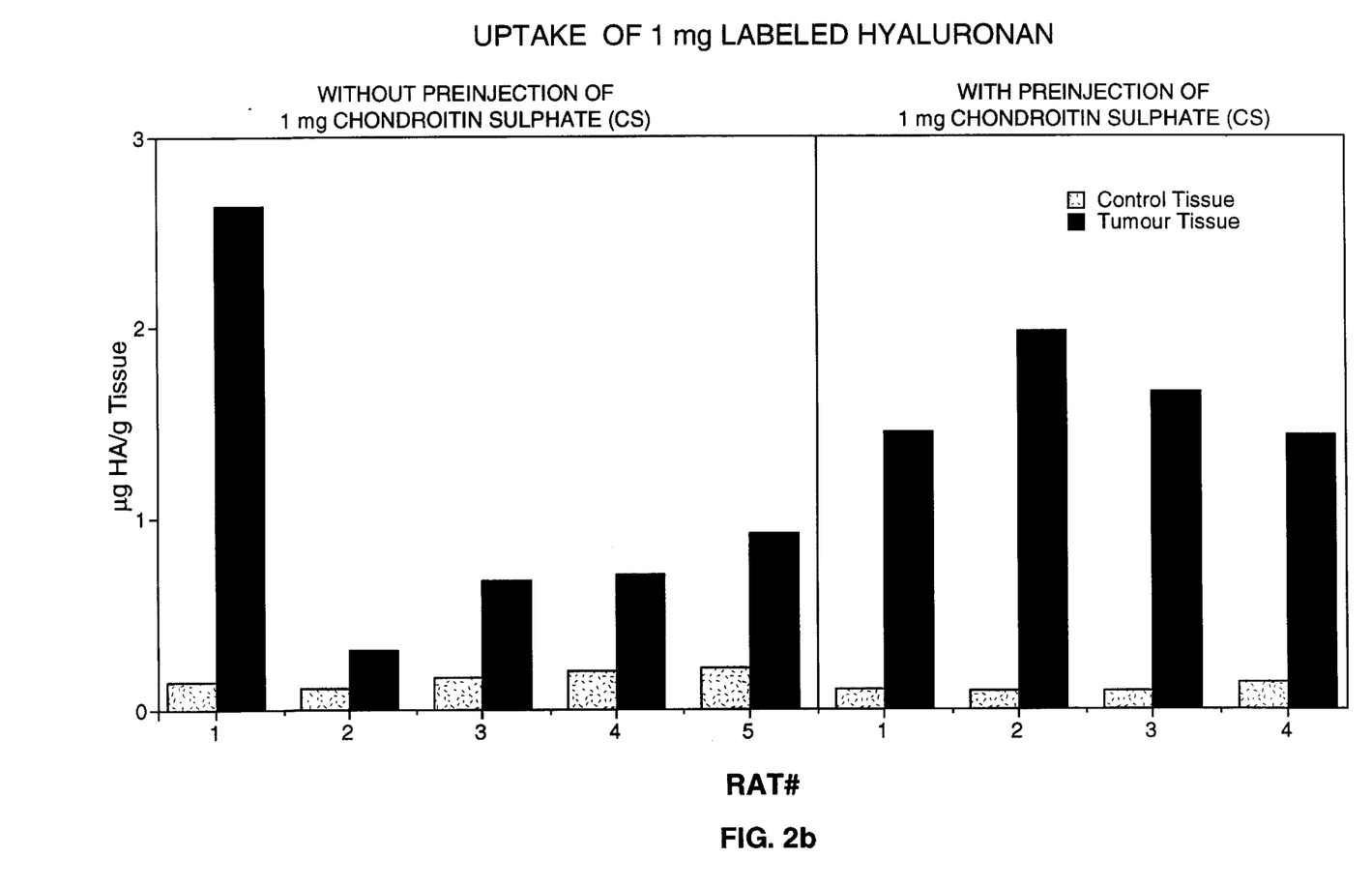
FIG. 2b illustrates the Uptake of 1 mg Labeled Hyaluronan.

Using chondroitin sulphate (CS) pretreatment the ratio is increased to 16.23+2.48. The increase is mainly due to a lower uptake in the non-tumour tissue (muscle of the healthy leg) but there is also a 27% increase in total amount bound (see FIG. 2).

Figure 3A:
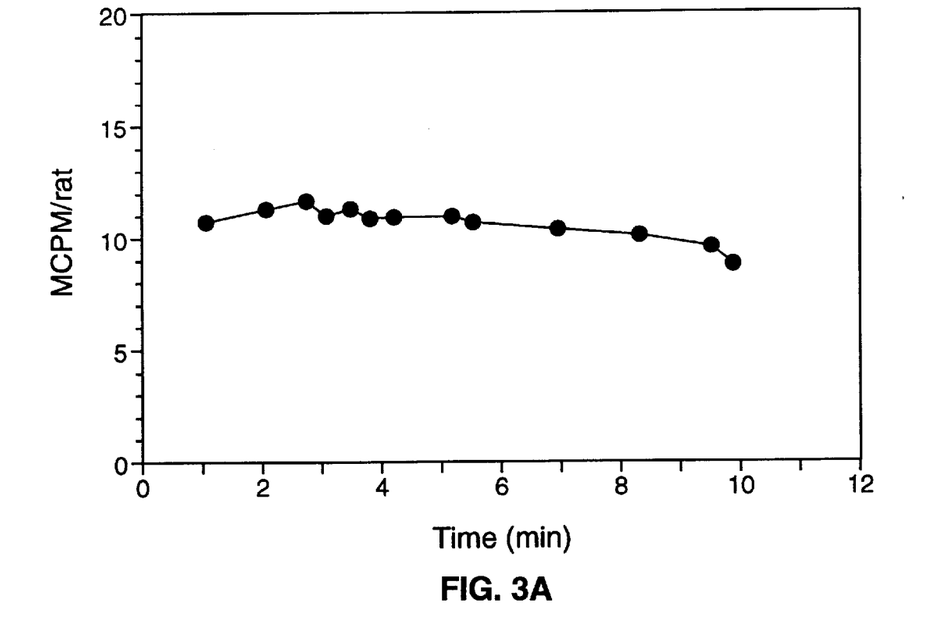
FIG. 3 is made up of two drawings, the top drawing comparing MCPM/rat v. Time (min.), and the lower drawing comparing the MCPM/organ when 1 mg of chondroitin sulphate was administered followed by $^{125}$I-HA ($^{125}$I-Hyaluronan).
Figure 3B:
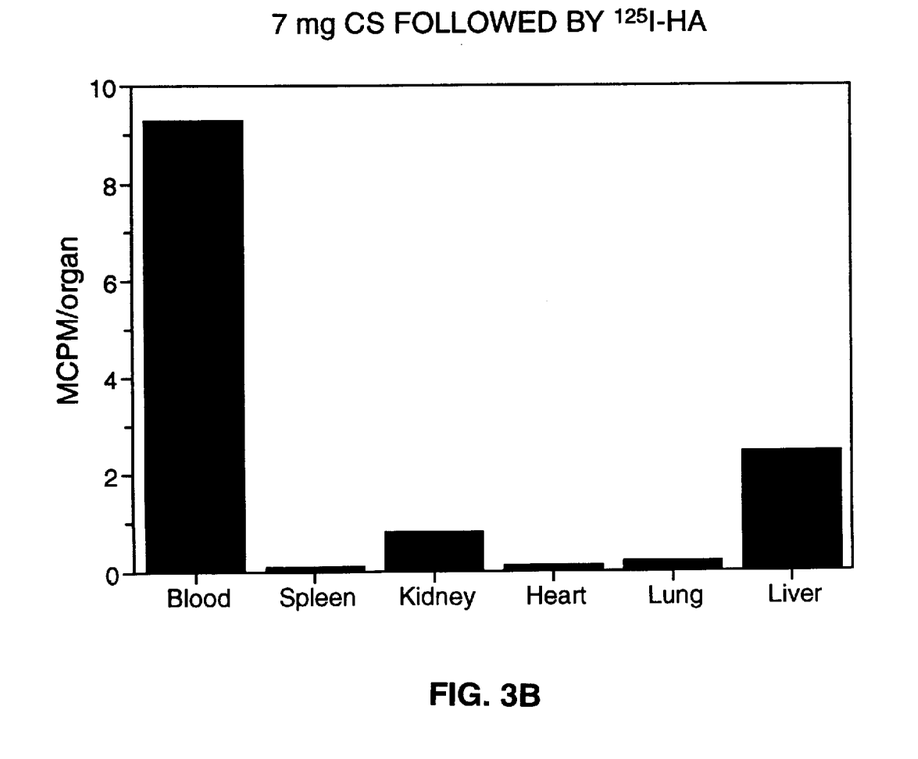

The individual values show that 4 out of 5 "controls" have a tumour to non-tumour ratio of about 4 (the relatively high ratio of 7.79 is due to one single experiment with a high ratio). In earlier published studies with labeled HA alone, I have seen tumour to non-tumour ratios of about 4 using similar, but not identical tumour systems. See "Accessible hyaluronan receptors identical to ICAM-1 in mouse mast cells", Stefan Gustafson, et al., Glycoconjugate Journal (1995) 12:350–355. Therefore, I have now developed a real improvement using chondroitin sulphate (CS) to the delivery of medicine and/or therapeutic agents. The administration of chondroitin sulphate (CS) effectively blocks liver uptake of labeled HA (hyaluronan) at 10–15 minutes by about 80% (see FIG. 3) (without chondroitin sulphate (CS) the liver would have absorbed 95% of the radioactivity at this time).

In vitro data also developed by me establishes the NGW tumour cells have HA (hyaluronan) take-up receptors that are not inhibited (blocked/immobilized for a period of time from taking up the second agent (for example, hyaluronan)) by chondroitin sulphate (CS).

Figure 4:
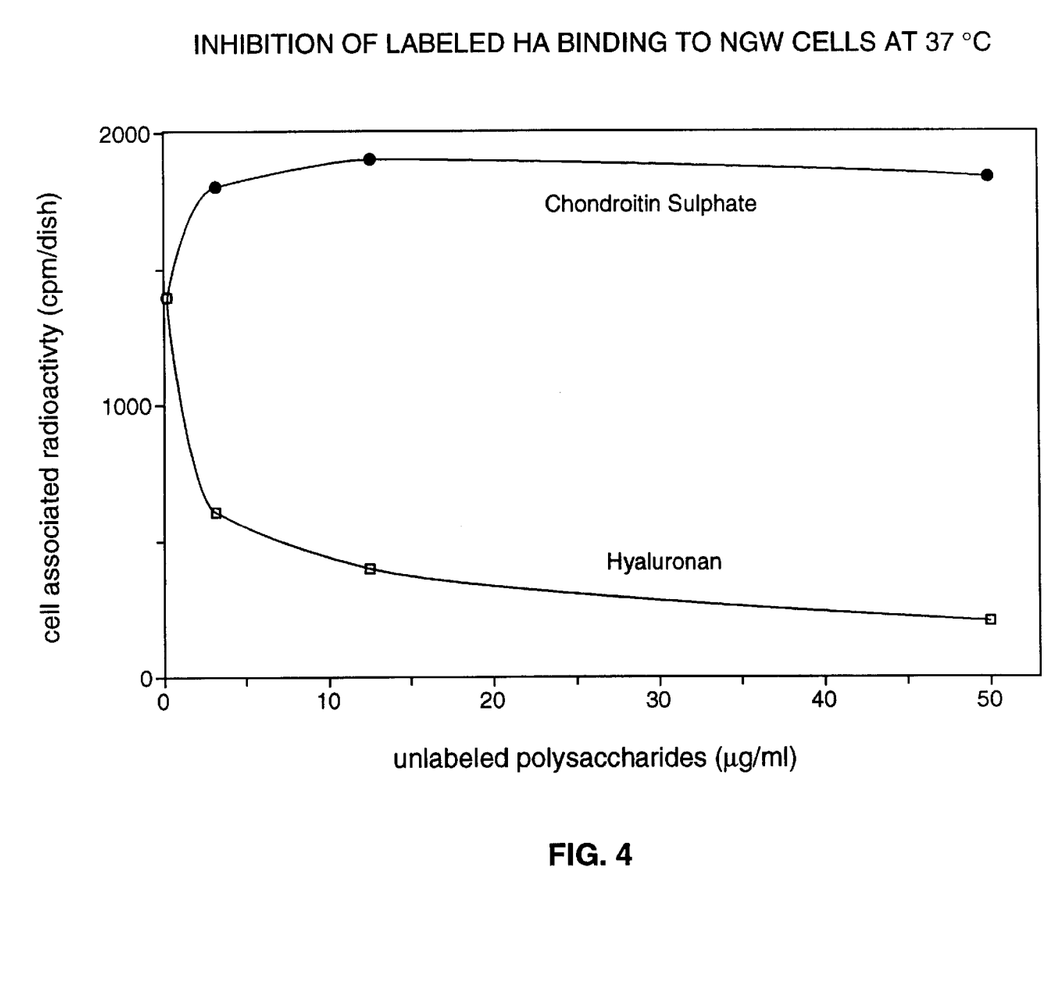
FIG. 4 illustrates the inhibition of labeled hyaluronan (HA) binding to NGW cells at 37 C. (The chondroitin sulphate does not interfere whereas the labeled hyaluronan does.)

FIG. 4 illustrates three determinations which clearly show that the uptake of radiolabelled hyaluronan is not interfered with by the chondroitin sulphate but is interfered with by the unlabeled hyaluronan.

Figure 5:
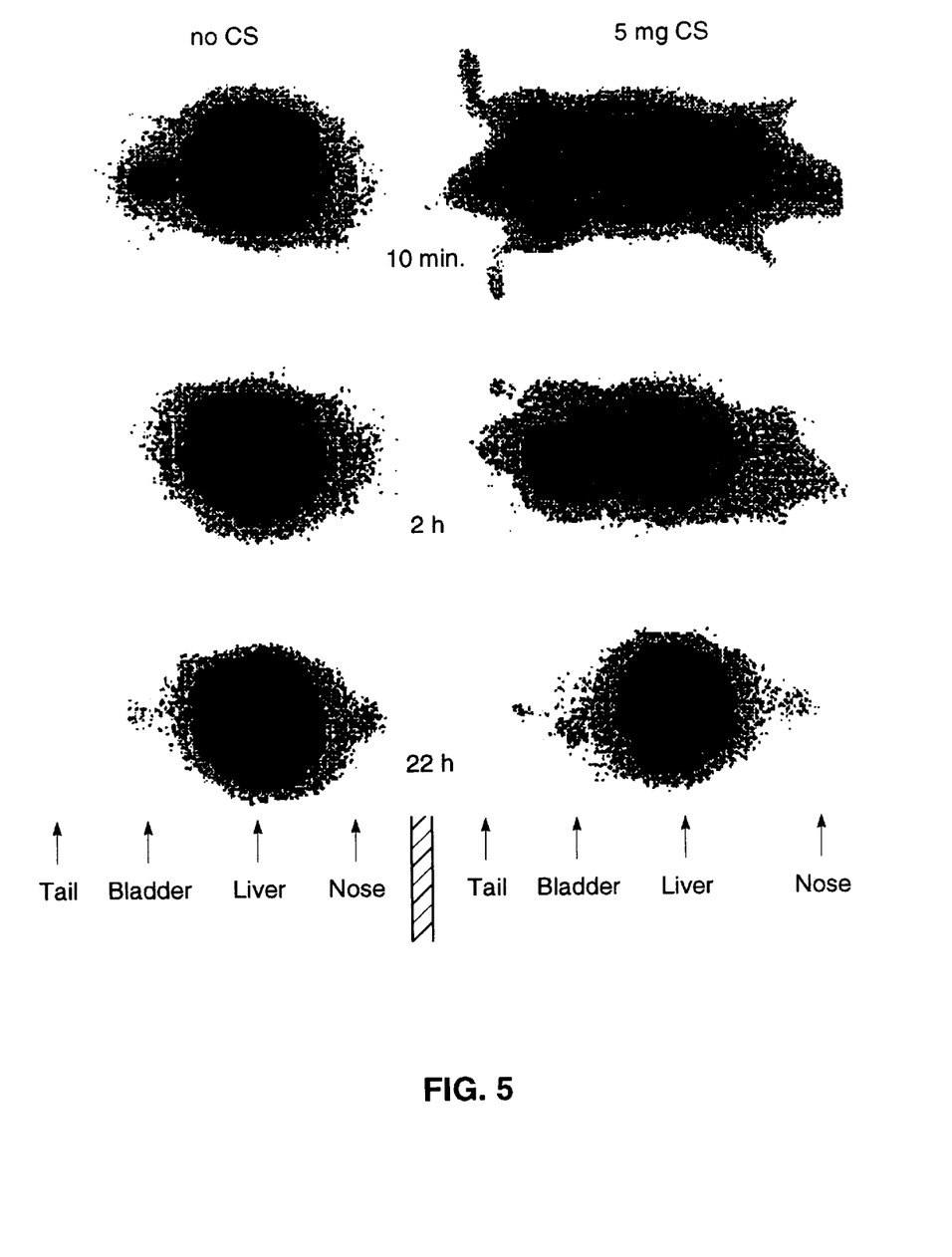
FIG. 5 show in vivo images of the reduced liver uptake of labeled hyaluronan (HA) after pre-treatment of rats by chondroitin sulphate (CS).

Composite FIG. 5 shows in vivo images of the reduced liver uptake of labeled HA after CS pre-treatment of rats. This figure shows that also uptake of trace amounts of HA (equivalent to 0.5–1 mg/70 kg person) can be effectively inhibited for an extended time by CS (equivalent dose 1–2 gm/70 kg person). Thus, one may use low amounts of not only active drug (medicine and/or therapeutic agent) (g/kg) but also of HA (g/kg of body weight of the patient). Thus, low amounts of HA (much less than 10 mg/70 kg person) can be used as the transport agent. Thus, I have developed a treatment whereby a low dose of HA and low dose of active drug (medicine and/or therapeutic agent) that really targets the site of treatment (for example diseased tissues) which is best has been provided and which also reduces side effects.

Figure 6:
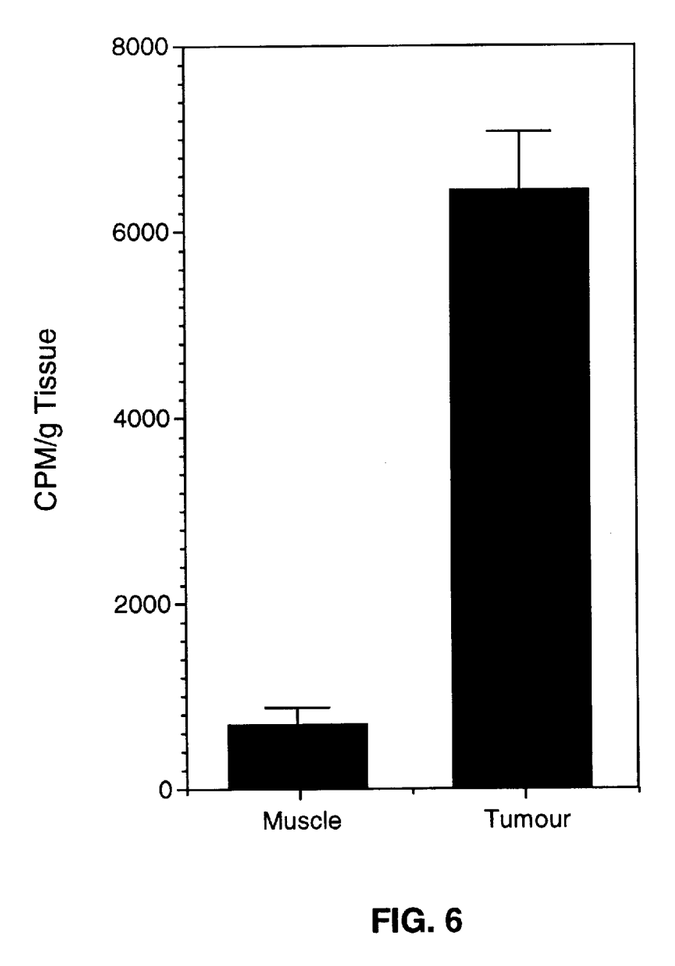
FIG. 6 illustrates the targeting of tumours by trace amount of labeled HA (hyaluronan) after administration of chondroitin sulphate (CS) in an effective amount of 200–400 mg/70 kg person of CS.

I have also performed experiments on tumour rats using 1 mg CS (200–400 mg/70 kg person) followed by a trace dose of labeled HA (equivalent to 0.5–1 mg/70 kg person) and seen good targeting to the tumour (see FIG. 6). The experimental conditions are identical to those previously described for NGW tumour rats, except for the low dose of HA. The relatively high radioactivity in the control muscle is most likely due to circulating degradation products at this time point (about 20 h after injection). Even so, the tumour to non-tumour ratio is 8.8 ($p<0.001$, $n=4$), showing that the targeting works also at lower HA doses.

Some preliminary size exclusion chromatographic studies were conducted on the Mw (molecular weight) distribution of radiolabeled HA (hyaluronan) in serum and urine of rats receiving a pretreatment of 5 mg CS and then 5 g 125I-HA (hyaluronan) with a molecular weight of about 400 kDa (400,000 daltons). Blood was collected at 2–4, 10–12, 22–24 and 70 minutes after the completion of the administration. Urine was collected from the bladder at 70 minutes when the animals were killed and organs collected. The results show that the Mw (molecular weight) of hyaluronan goes down (reduces in the body) by time and at 70 minutes, most of the hyaluronan that is left in the circulation has a molecular weight less than 39 kDa (39,000 daltons). At this time, about 10% of the injected radioactivity was found in the urine and had a mean Mw (molecular weight) of about 20 kDa (20,000 daltons). The radioactivity in the liver was only 6–7% while kidneys contained about 9%, I believe, due to material being filtered out into urine. Blood contained around 35% and as other organs contained only negligible amounts, about 40% has been filtered out into peripheral tissues. The chondroitin sulphate (CS) blocking is therefore an ideal way of getting some hyaluronan out into the tissues. This is an additional factor in the increased binding of intravenously administered hyaluronan (HA) to tumour tissue that I found using chondroitin sulphate pretreatment. This provides a further method of delivering a form of hyaluronan (HA) together with a medicine and/or therapeutic agent into interstitial fluid, lymph and lymph nodes for the treatment of disease for example, cancer and metastases. This treatment may also be used to prevent metastases.

As many changes can be made to the embodiments without departing from the scope of the invention, it is intended that all material contained herein be interpreted as illustrative of the invention and not in a limiting sense.

The embodiments of the invention from which an exclusive property of privilege is claimed are as follows:

1. A method of treating a disease or condition in a human treatable by a medicinal or therapeutic agent which may be transported by an agent to the site in need of treatment in the body and which agent may also transport the medicinal or therapeutic agent to the liver comprising:

(a) administering an effective non-toxic amount of a first agent which does not bind to receptors at the site in need of treatment but which binds with receptors of the liver thereby "down regulating" the liver, wherein the first agent selected from glycosaminoglycans, except forms of hyaluronic acid; Keratan sulphate; and acetylated low density lipoproteins: and, (b) thereafter administering during the time the liver receptors are down-regulated by the first agent, an effective non-toxic amount of a medicinal or therapeutic agent and an effective amount of a second agent which is a transport agent and is a different agent from the first agent and which second agent binds to the site in need of treatment and would be capable of binding to the sites of the liver if the liver had not been "down regulated" so that its binding capacity for the second agent has been substantially reduced by the up-take by the liver of the first agent administered under sub-paragraph (a) by binding with the scavenger receptors of the liver, wherein the second agent is selected from a form of hyaluronic acid.

2. The method of claim 1 wherein the first agent is a glycosaminoglycan which is not a form of hyaluronic acid having a molecular weight less than 750,000 daltons.

3. The method of claim 1 wherein the first agent is chondroitin sulphate.

4. The method of claim 3 wherein the second agent (transport agent) is a form of hyaluronic acid having a molecular weight less than 750,000 daltons.

5. The method of claim 4 wherein the form of hyaluronic acid is selected from the group consisting of hyaluronic acid (hyaluronan) and a pharmaceutically acceptable salt thereof.

6. The method of claim 4 wherein the amount of chondroitin sulphate exceeds about 3–5 mg./kg of the human.

7. The method of claim 1, 3, or 6 wherein the second agent is an effective amount of the form of hyaluronic acid having a molecular weight less than 750,000 daltons.

8. A method of protecting the liver from taking up medicinal or therapeutic agents toxic to the liver and which are to be administered to a patient comprising:
 (a) administering an effective amount of a first agent which does not bind to receptors at the site in need of treatment but which binds with receptors of the liver thereby "down regulating" the liver, wherein the first agent selected from glycosaminoglycans, except forms of hyaluronic acid; Keratan sulphate; and acetylated low density lipoproteins; and,
 (b) thereafter administering during the time the liver receptors are down-regulated by the first agent, an effective amount of a medicinal or therapeutic agent and an effective amount of a second agent which is a transport agent and is a different agent from the first agent and which second agent is a transport agent which binds to the site in need of treatment and would be capable of binding to the sites of the liver if the liver had not been "down regulated" so that its binding capacity for the second agent has been substantially reduced by the up-take by the liver of the first agent administered under sub-paragraph (a) by binding with the scavenger receptors of the liver, said second agent being selected from a form of hyaluronic acid.

9. The method of claim 8 wherein the first agent is chondroitin sulphate and the second agent is a form of hyaluronic acid.

10. The method of claim 9 wherein the form of hyaluronic acid is selected from the group consisting of hyaluronic acid and pharmaceutically acceptable salts thereof having a molecular weight less than 750,000 daltons.

11. The method of claim 10 wherein the amount of chondroitin sulphate exceeds 3–5 mg./kg.

12. The method of claim 11 wherein the effective amount of the form of hyaluronic acid exceeds 0.1 mg.

13. The method of claim 8 or 9 wherein the effective amount of the form of hyaluronic acid has a molecular weight less than 750,000 daltons.

14. A dosage kit for maximizing the amount of medicinal or therapeutic agent to be delivered to a site in the body in need of treatment and for protecting the liver from taking up the medicinal or therapeutic agent when the medicinal or therapeutic agents must be delivered to treat sites other than the liver, comprising:
 (a) an effective dosage amount of a first agent which does not bind to receptors at the site in need of treatment but which binds with receptors of the liver to thereby "down regulate" the liver, wherein the first agent selected from glycosaminoglycans, except forms of hyaluronic acid; Keratan sulphate; and acetylated low density lipoproteins;
 (b) a separate effective dosage amount, separate from the dosage amount in subparagraph (a), comprising an effective non-toxic amount of a medicinal or therapeutic agent and an effective amount of a second agent which is a transport agent and is a different agent from the first agent and which second agent binds to the site in need of treatment and would be capable of binding to the sites of the liver if the liver is not down regulated so that its binding capacity for the second agent has been substantially reduced by the up-take by the liver of the first agent when the second agent is administered after the dosage amount under sub-paragraph (a) is administered, said second agent being selected from a form of hyaluronic acid.

15. The dosage kit of claim 14 wherein the first agent is chondroitin sulphate and the second agent is a form of hyaluronic acid.

16. The dosage kit of claim 15 wherein the form of hyaluronic acid is selected from the group consisting of hyaluronic acid and pharmaceutically acceptable salts thereof having a molecular weight less than 750.000 daltons.

17. The dosage kit of claim 16 wherein the amount of chondroitin sulphate exceeds about 3–5 mg. of the body.

18. The dosage kit of claim 17 wherein the amount of the form of hyaluronic acid exceeds 0.1 mg.

19. The dosage kit of claim 14 or 15 wherein the form of hyaluronic acid has a molecular weight less than 750,000 daltons.

20. A method of treating a disease or condition in a human treatable by a medicinal or therapeutic agent which may be transported by an agent to the site in need of treatment in the body and which agent may also transport the medicinal or therapeutic agent to the liver comprising:
 (a) administering an effective non-toxic amount of a first agent which does not bind to receptors at the site in need of treatment but which binds with receptors of the liver thereby "down regulating" the liver, wherein the first agent selected from glycosaminoglycans, except forms of hyaluronic acid; Keratan sulphate; and acetylated low density lipoproteins; and,
 (b) thereafter administering during the time the liver receptors are down-regulated by the first agent, an effective non-toxic amount of a medicinal or therapeutic agent which is substantially less than the amount normally considered effective and an effective amount of a second agent which is a transport agent and is a different agent from the first agent and which second agent would bind to the site in need of treatment and would be capable of binding to the sites of the liver if the liver had not been "down regulated" so that its binding capacity for the second agent has been substantially reduced by the up-take by the liver of the first agent administered under sub-paragraph (a) by binding with the scavenger receptors of the liver and which effective non-toxic amount of the second agent is in an effective amount which is substantially less than the amount normally considered effective, wherein the second agent is selected from a form of hyaluronic acid.

21. The method of claim 20 wherein the first agent is a glycosaminoglycan which is not a form of hyaluronic acid.

22. The method of claims 20 or 21 wherein the first agent is chondroitin sulphate.

23. The method of claim 22 wherein the second agent (transport agent) is a form of hyaluronic acid having a molecular weight less than 750,000 daltons.

24. The method of claim 23 wherein the form of hyaluronic acid is selected from the group consisting of hyaluronic acid (hyaluronan) and a pharmaceutically acceptable salt thereof having a molecular weight less than 750,000 daltons and greater than 150,000 daltons.

25. The method of claim 23 wherein the amount of chondroitin sulphate exceeds about 3–5 mg./kg of the human.

26. The method of claim 20 or 25 wherein the second agent is an effective amount exceeding about 20 μg/kg of body weight of the patient of the form of hyaluronic acid having a molecular weight less than 750,000 daltons.

27. A method of protecting the liver from taking up medicinal or therapeutic agents toxic to the liver comprising:
 (a) administering an effective amount of a first agent which does not bind to receptors at the site in need of treatment but which binds with receptors of the liver thereby "down regulating" the liver, wherein the first agent selected from glycosaminoglycans, except forms of hyaluronic acid; Keratan sulphate; and acetylated low density lipoproteins; and,
 (b) thereafter administering during the time the liver receptors are down-regulated by the first agent, an effective amount of a medicinal or therapeutic agent which is substantially less than the amount normally used and an effective amount of a second agent which is a transport agent and is a different agent from the first agent and which second agent is a transport agent which binds to the site in need of treatment and would be capable of binding to the sites of the liver if the liver had not been "down regulated" so that its binding capacity for the second agent has been substantially reduced by the up-take by the liver of the first agent administered under sub-paragraph (a) by binding with the scavenger receptors of the liver and which effective amount of the second agent is in an effective amount which is substantially less than the amount normally considered effective, wherein the second agent is selected from a form of hyaluronic acid.

28. The method of claim 27 wherein the first agent is chondroitin sulphate and the second agent is a form of hyaluronic acid.

29. The method of claim 28 wherein the form of hyaluronic acid is selected from the group consisting of hyaluronic acid and pharmaceutically acceptable salts thereof having a molecular weight less than 750,000 daltons.

30. The method of claim 29 wherein the amount of chondroitin sulphate exceeds 3–5 mg./kg.

31. The method of claim 30 wherein the effective amount of the form of hyaluronic acid exceeds 0.1 mg.

32. The method of claim 27 or 30 wherein the effective amount of the form of hyaluronic acid has a molecular weight less than 750,000 daltons and is an amount exceeding about 20 μg/kg of body weight of a patient.

33. A dosage kit for maximizing the amount of medicinal or therapeutic agent to be delivered to a site in the body in need of treatment and for protecting the liver from taking up the medicinal or therapeutic agent when medicinal or therapeutic agents must be delivered to treat sites other than the liver, comprising:
 (a) an effective dosage amount of a first agent which does not bind to receptors at the site in need of treatment but which binds with receptors of the liver to thereby "down regulate" the liver, wherein the first agent selected from glycosaminoglycans, except forms of hyaluronic acid; Keratan sulphate; and acetylated low density lipoproteins;
 (b) a separate effective dosage amount, separate from the dosage amount in subparagraph (a) comprising an effective non-toxic amount of a medicinal or therapeutic agent which is substantially less than the amount normally considered effective and an effective amount of a second agent which is a transport agent and is a different agent from the first agent and which second agent would bind to the site in need of treatment and would be capable of binding to the sites of the liver if the liver is not down regulated so that its binding capacity for the second agent has been substantially reduced by the up-take by the liver of the first agent when administered after the dosage amount under sub-paragraph (a) is administered and which effective non-toxic amount of the second agent is in an effective amount which is substantially less than the amount normally considered effective, wherein the second agent is selected from a form of hyaluronic acid.

34. The dosage kit of claim 33 wherein the first agent is chondroitin sulphate and the second agent is a form of hyaluronic acid.

35. The dosage kit of claim 34 wherein the form of hyaluronic acid is selected from the group consisting of hyaluronic acid and pharmaceutically acceptable salts thereof having a molecular weight less than 750,000 daltons.

36. The dosage kit of claim 35 wherein the amount of chondroitin sulphate exceeds about 3–5 mg.

37. The dosage kit of claim 36 wherein the amount of the form of hyaluronic acid exceeds 0.1 mg.

38. The dosage kit of claim 33 or 36 wherein the effective amount of the form of hyaluronic acid has a molecular weight less than 750,000 daltons.

39. A method of preventing metastases in a person suffering from cancer comprising:
 (a) administering an effective amount of a first agent which does not bind to receptors at the site in need of treatment but which binds with receptors of the liver thereby "down regulating" the liver, wherein the first agent selected from glycosaminoglycans, except forms of hyaluronic acid; Keratan sulphate; and acetylated low density lipoproteins; and,
 (b) thereafter administering during the time the liver receptors are down-regulated by the first agent, an effective amount of a medicinal or therapeutic agent and an effective amount of a second agent which is a transport agent and is a different agent from the first agent and which second agent is a transport agent which binds to the site in need of treatment and transports to the interstitial fluid, lymph and nodes and would be capable of binding to the sites of the liver if the liver had not been "down regulated" so that its binding capacity for the second agent has been substantially reduced by the up-take by the liver of the first agent administered under sub-paragraph (a) by binding with the scavenger receptors of the liver, wherein the second agent is selected from a form of hyaluronic acid.

40. The method of claim 39 wherein the first agent is chondroitin sulphate and the second agent is a form of hyaluronic acid.

41. The method of claim 40 wherein the form of hyaluronic acid is selected from the group consisting of hyaluronic acid and pharmaceutically acceptable salts thereof having a molecular weight less than 750,000 daltons.

42. The method of claim 41 wherein the amount of chondroitin sulphate exceeds 3–5 mg./kg.

43. The method of claim 42 wherein the effective amount of the form of hyaluronic acid exceeds 0.1 mg.

44. The method of claim 39 or 40 wherein the effective amount of the form of hyaluronic acid has a molecular weight less than 750,000 daltons.

45. The method of claim 39, 40, 41 or 42, wherein the medicinal or therapeutic agent is selected from the group consisting of a non-steroidal anti-inflammatory drug (NSAID) and a cytotoxic agent and combinations thereof.

* * * * *